United States Patent [19]

Schrinner et al.

[11] Patent Number: 5,055,457

[45] Date of Patent: Oct. 8, 1991

[54] PHARMACEUTICAL COMBINATIONS PRODUCT AND THE PREPARATION AND USE THEREOF

[75] Inventors: Elmar Schrinner, Wiesbaden; Irvin Winkler, Liederbach; Christoph Meichsner, Hofheim am Taunus; Matthias Helsberg, Kelkheim, all of Fed. Rep. of Germany

[73] Assignee: Hoechst Aktiengesellschaft, Frankfurt am Main, Fed. Rep. of Germany

[21] Appl. No.: 226,250

[22] Filed: Jul. 29, 1988

[30] Foreign Application Priority Data

Aug. 1, 1987 [DE] Fed. Rep. of Germany ....... 3725554

[51] Int. Cl.⁵ ..................... A61K 31/715; C08B 37/00
[52] U.S. Cl. ........................................ 514/59; 514/54; 536/55.3
[58] Field of Search ............. 514/54, 59, 263, 265, 514/264; 544/267, 270, 272, 271, 268; 536/55.3

[56] References Cited

U.S. PATENT DOCUMENTS

| | | | |
|---|---|---|---|
| 3,175,942 | 3/1965 | Anderson et al. | 514/54 |
| 4,108,995 | 8/1978 | Mohler et al. | 514/263 |
| 4,533,493 | 8/1985 | Benovic et al. | 435/7 |
| 4,783,446 | 11/1988 | Neushul | 514/54 |

FOREIGN PATENT DOCUMENTS

| | | | |
|---|---|---|---|
| 42706 | 12/1981 | European Pat. Off. | 514/263 |
| 0270317 | 11/1987 | European Pat. Off. | |
| 2364373 | 12/1973 | Fed. Rep. of Germany | |

OTHER PUBLICATIONS

K. Maramorosch and H. Koprowski, "Methods in Virology," VI:59–108.
De Clercq & Balzarini, Antiviral Res. Suppl. (1985), pp. 89–94.
R. Yarshoan et al., The Lancet (1986).

*Primary Examiner*—Ronald W. Griffin
*Assistant Examiner*—Everett White
*Attorney, Agent, or Firm*—Finnegan, Henderson, Farabow, Garrett, and Dunner

[57] ABSTRACT

A pharmaceutical combination product containing or composed of
a) at least one sulfated polysaccharide and
b) at least one xanthine derivative.

The product is suitable for controlling and preventing virus diseases, especially those caused by retroviruses.

14 Claims, No Drawings

PHARMACEUTICAL COMBINATIONS PRODUCT AND THE PREPARATION AND USE THEREOF

DESCRIPTION

The basis for the search aimed at substances having antiviral activity is the existence of virus-specific metabolic processes in the infected organism. The retroviruses, which include HIV (human immunodeficiency virus), require during the course of the infection cycle the activity of a RNA-dependent DNA polymerase to transcribe their genetic information, which is coded in the form of an RNA, into a DNA which can be integrated into the host genome and can be converted by appropriate host enzymes into active gene products. The enzyme which is called reverse transcriptase (RT) is a constituent of the infecting virus particle and is not normally found in the human or animal organism. Hence RT appears to be a suitable point of attack by a chemotherapy of retroviral diseases and thus also of acquired immunodeficiency syndrome (AIDS) which represents the late consequence of an infection by HIV.

It is known that sulfated polysaccharides are able to inhibit the growth of retroviruses in cell cultures (Klement & Nicolson in Mormorosch & Koprowski, Methods in Virology VI, (1977) 60–103). These substances are highly effective inhibitors of RT. An example of these substances is pentosan polysulfate—a 1,4-linked pyranose polymer having up to 2 sulfate groups per sugar unit; i.e. a compound of the following formula:

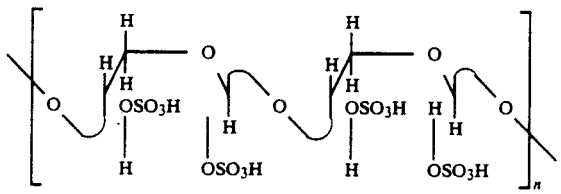

n = number of structural units

Side effects of this compound include inhibition of blood coagulation and impairment of hair growth.

A number of other substances which inhibit various steps in the reaction catalyzed by RT is known (De Clerq & Balzarini: Antiviral Research Suppl. 1 (1985) 89–94). Some of these which have been tested clinically to date, with little success, are suramin, a compound of the formula

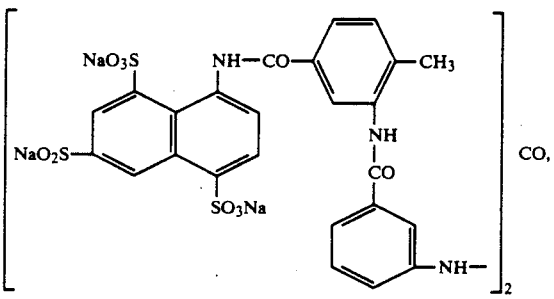

polyantimonotungstic acid $((NH_4)_{18}(NaW_{21}Sb_9O_{86})_{17})$ and phosphonoformic acid $((OH)_2(O)PCOOH)$. The first compound to have confirmed therapeutic success in clinical trials was the synthetic nucleoside 3'-azido-3'-deoxythymidine (AZT), of the formula

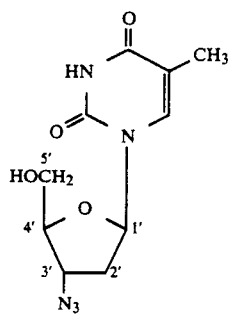

(Yarchoan et al.: The Lancet 575–580 (1986)), but the flaw is that it is associated with serious side effects which do not permit the chronic therapy which is necessary according to present knowledge.

It has now been found, surprisingly, that the efficacy of the sulfated polysaccharides can be distinctly increased by concomitant administration of at least one xanthine derivative.

Xanthine is the compound of the formula:

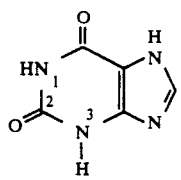

The combination with xanthine derivatives means that the sulfated polysaccharides can be administered in a smaller quantity than without the said xanthine derivatives in order to achieve the same effect. A dosage form of this type has the advantage that the side effects of the sulfated polysaccharide are correspondingly reduced. The said dosage form is suitable for chronic therapy.

Accordingly, the invention relates to a pharmaceutical combination product which contains, as component a), at least one sulfated polysaccharide and, as component b), at least one xanthine derivative, or is composed of these components. In this connection, the sulfated polysaccharide can be in the form of the free acid, i.e. with the O—SO$_3$H group, or in the form of a physiologically tolerated salt, preferably an ammonium or alkali metal salt, i.e. with the O—SO$_3$A group (A=ammonium or alkali metal).

For carrying out the invention, it is possible in principle for any desired sulfated polysaccharide to be used as sulfated polysaccharide for component a). Preferred compounds are dextran polysulfate, levan polysulfate and pentosan polysulfate, especially pentosan polysulfate.

The mean molecular weight of the sulfated polysaccharides can extend over a wide range. A range of about 1,000 to 20,000 Dalton is preferred, particularly preferably of about 5,000 to 12,000 Dalton, especially of about 6,000 Dalton.

The degree of sulfation of the polysaccharide OH groups, i.e. the average number of sulfate radicals per monosaccharide unit, can vary within wide limits. The degree of sulfation of the polysaccharide OH groups is preferably in a range of about 20 to 100% of the OH groups present, particularly preferably of about 80 to 95%, especially of about 90%.

It is possible in principle for any desired xanthine derivatives or mixtures thereof to be used for component b) of the combination products according to the invention. Preferred xanthine derivatives originate from the group of the following compounds:

b1) compounds of the formula I

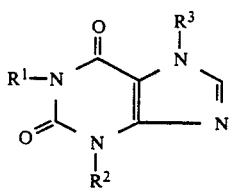
(I)

in which one of the radicals $R^1$ and $R^3$ represents a straight-chain alkyl, ($\omega$-1)-oxoalkyl or ($\omega$-1)-hydroxyalkyl group having 3 to 8 carbon atoms, and the two other radicals $R^2$ and $R^3$, or $R^1$ and $R^2$, represent straight-chain or branched alkyl groups having 1 to 8 carbon atoms in the position of $R^1$ and $R^3$, and 1 to 4 carbon atoms in the position of $R^2$, with the total of carbon atoms in these two alkyl substituents being not more than 10, b2) compounds of the formula II

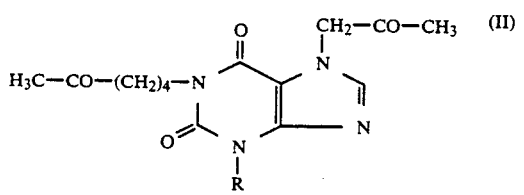
(II)

in which R represents an alkyl radical having 1 to 4 carbon atoms, b3) compounds of the formula III

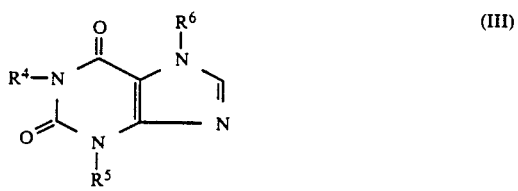
(III)

in which at least one of the radicals $R^4$ and $R^6$ represents a tertiary hydroxyalkyl group of the formula

(IIIa)

where $R^7$ denotes an alkyl group having up to 3 carbon atoms, and n denotes an integer from 2 to 5 and—if only one of the radicals $R^4$ or $R^6$ denotes such a tertiary hydroxyalkyl group of the formula IIIa—the other radical represents a hydrogen atom or an aliphatic hydrocarbon radical $R^8$ which has up to 6 carbon atoms and whose carbon chain can be interrupted by up to 2 oxygen atoms or substituted by an oxo group or up to two hydroxyl groups (with an oxo or hydroxyl group present in the radical $R^8$ preferably being separated from the nitrogen by at least 2 carbon atoms), and $R^5$ represents an alkyl group having 1 to 4 carbon atoms, b4) prodrug forms of the compounds of the formulae I to III and/or b5) metabolites of the compounds of the formulae I to III.

Among these compounds, those of the formula I which are in turn particularly preferred have a hexyl, 5-oxohexyl or 5-hydroxyhexyl group in the position of $R^1$ or $R^3$. These include, in particular, 1-hexyl-3,7-dimethylxanthine,
1-(5-hydroxyhexyl)-3,7-dimethylxanthine,
3,7-dimethyl-1-(5-oxohexyl)xanthine,
7-(5-hydroxyhexyl)-1,3-dimethylxanthine,
1,3-dimethyl-7-(5-oxohexyl)xanthine,
1-(5-hydroxyhexyl)-3-methyl-7-propylxanthine and
3-methyl-1-(5-oxohexyl)-7-propylxanthine, especially
3,7-dimethyl-1-(5-oxohexyl)xanthine (=pentoxifylline).

Particularly preferred compounds of the formula III are those compounds in which $R^5$ represents a methyl or ethyl group. Equally preferred are those compounds of the formula III in which only one of the two radicals $R^4$ or $R^6$ represents the tertiary hydroxyalkyl group defined above. Also preferred are those compounds in which $R^7$ represents a methyl group, and n denotes an integer from 3 to 5, so that the tertiary hydroxyalkyl radical IIIa represents either [($\omega$-1)-hydroxy-($\omega$-1)-methyl]-pentyl, -hexyl or -heptyl, especially those in which $R^5$ denotes methyl or ethyl.

Furthermore, particular emphasis is to be placed on those compounds of the formula III in which $R^4$ represents a tertiary hydroxyalkyl group, and $R^6$ represents alkyl, hydroxyalkyl or alkoxyalkyl, having 1 to 4 carbon atoms in each case, such as, for example, 7-ethoxymethyl-1-(5-hydroxy-5-methylhexyl)-3-methylxanthine.

A further embodiment of the invention comprises using the oxoalkylxanthines of the formulae I and II, or the hydroxyalkylxanthines of the formulae I and III, not as such but in prodrug form, from which the therapeutically effective xanthine compounds having the substituents defined in formulae I, II and III can be liberated only by biotransformation in the organism. Suitable for this purpose are, for example, the acetalized oxoalkylxanthines, in which the carbonyl groups are replaced by the structural element of the formula IV

(IV)

and the 0-acylated hydroxyalkylxanthines having the structural element of the formula (V)

(V)

in place of the hydroxyl group, with $R^9$ and $R^{10}$ representing in each case an alkyl group having up to 4 carbon atoms, or together representing an ethylene, trimethylene or tetramethylene group, and $R^{11}$ denoting an alkyl radical having up to 4 carbon atoms or optionally substituted phenyl or pyridyl.

The ratio by weight of component a) to component b) in the combination products according to the invention can extend over a wide range. Preference is to be given to a ratio by weight of component a) to component b) of about 1:100 to about 100:1, particularly preferably of about 1:10 to 30:1.

The combination products according to the invention can be administered in a variety of ways for the treatment or for the prophylaxis of diseases caused by viruses—especially by retroviruses. For example, they can be administered intravenously, intramuscularly, intraperitoneally, subcutaneously, as a continuous drip, or orally. In acute pathological states, administration as a continuous drip is to be preferred. Oral administration is indicated for chronic medication.

The combination products according to the invention are prepared by converting at least one sulfated polysaccharide and at least one xanthine derivative, where appropriate with further additives and/or auxiliaries, into a suitable dosage form. The additives or auxiliaries originate from the group of vehicles, preservatives and other customary auxiliaries. Examples of auxiliaries which can be used for oral dosage forms are starch, for example potato, corn or wheat starch, cellulose or derivatives thereof, especially microcrystalline cellulose, silicon dioxide, various sugars such as lactose, magnesium carbonate and/or calcium phosphates. It is furthermore advantageous to add to the oral dosage forms auxiliaries which improve the tolerability of the medicaments, such as, for example, mucilaginous agents and resins. It is also possible, to improve the tolerability, to administer the medicaments in the form of enteric capsules. Furthermore, it may be advantageous to add to the dosage form, or to one component of the combination product, an agent to slow release, where appropriate in the form of permeable membranes such as, for example, those based on cellulose or polystyrene resin, or ion exchangers.

The dosage of the combination products according to the invention which is to be used depends on various factors such as the dosage form of the medicament and the condition and weight of the patient. However, a daily dose of about 800 mg of sulfated polysaccharide and about 800 mg of a xanthine derivative should be exceeded only short-term. About 100 to 600 mg of sulfated polysaccharide and about 75 to 600 mg of xanthine derivative are preferred, in each case as daily dose. It is furthermore expedient to test experimentally both the composition and the dosage of specific combinations of active substances. These experiments can be carried out in vitro (cf., for example, the efficacy test I described hereinafter) and in vivo (cf., for example, the efficacy test II described hereinafter).

The active substances required for the combination products according to the invention can be prepared in the following way:

1. Sulfated polysaccharides of component a)

The sulfated polysaccharides, some of which are also commercially available products (for example pentosan polysulfate SP 54, mean molecular weight about 600 Dalton, degree of sulfation about 90%, manufactured by bene-Chemie GmbH, 8000 Munich 71, Herterichstrasse 1), can be prepared in the following way, for example (R. L. Whistler, Meth. Carbohydr. Chem. IV, 426–429 (1972)): initially a DMSO/sulfur trioxide complex is prepared by dropwise addition of sulfur trioxide at about 15° C. to 17° C. to about 4 times the volume of stirred DMSO. A solvent, preferably methylene chloride (preferably 4 times the volume of the sulfur trioxide), is then added. The resulting solid complex can be removed by filtration and can then be dried. The polysaccharide to be sulfated (obtainable, for example, as stated in Meth. Carbohydr. Chem. IV (1972) [1]–[4], [7] is dissolved in a solvent, for example DMSO, and the complex obtained as described above is added at a temperature of, preferably, about 15° C. to 17° C. The amount of complex needed for a particular degree of sulfation should be determined empirically for each polysaccharide. After ice-water has been added and the solution has been neutralized with alkali metal hydroxide, the sulfated product can be precipitated, for example by addition of methanol. It is expedient to purify the resulting product further; particularly advantageous purification processes are chromatographic separation and gel filtration, which also allows separation as a function of the degree of sulfation and molecular weight.

2. Xanthine derivatives of component b)

The xanthine derivatives, some of which are likewise commercially available products (for example ®Trental, active substance pentoxifylline, from Hoechst AG, Frankfurt), can be prepared, for example, as described for various specific compounds in DE-B 1,233,405 or DE-B 1,235,320.

The preparation examples which follow are intended to illustrate the invention in detail.

EXAMPLE 1

Tablets which are suitable for oral administration and contain the following components are prepared in a manner known per se by the active substances and auxiliaries being granulated and then compressed to form tablets. These tablets are suitable for antiviral treatment in a dose of one tablet 3–4 times a day.

| Constituents (per tablet) | Weight |
|---|---|
| Pentosan polysulfate, Na Salt | 100 mg |
| Mean molecular weight 6,000 Dalton | 50 mg |
| Degree of sulfation 90% | |
| Pentoxifylline | |
| Lactose | 150 mg |
| Corn Starch | 50 mg |
| Talc | 6 mg |
| Colloidal silicon dioxide | 6 mg |
| Magnesium stearate | 4 mg |

EXAMPLE 2

Capsules suitable for oral administration contain the constituents stated below and can be prepared in a manner known per se by the active substances and auxiliaries being mixed and dispensed into gelatin capsules. These capsules are used for antiviral treatment in a dose of one capsule 2–4 times a day.

| Constituents (per capsule) | Weight |
|---|---|
| Pentosan polysulfate, Na Salt | 150 mg |
| Mean molecular weight 6,000 Dalton, | 75 mg |
| Degree of sulfation 90% | |
| Pentoxifylline | |
| Lactose | 200 mg |
| Talc | 10 mg |
| Colloidal silicon dioxide | 10 mg |

EXAMPLE 3

Active substance solutions suitable for injection contain the constituents stated below and can be prepared in a manner known per se by the substances being mixed together and dispensed into sterile ampules which are closed with a rubber cap. The injection solutions are used for antiviral treatment in a dose of 1-2 injection units (1 injection unit = 1 ampule) per day.

| Constituents (per ampule) | Weight |
|---|---|
| Pentosan polysulfate, Na salt | 150 mg |
| Mean molecular weight 6,000 Dalton, Degree of sulfation 90% | |
| Pentoxifylline | 25 mg |
| Sodium chloride | 50 mg |
| Methylparaben | 5 mg |
| Sterile water | 5 mg |

EFFICACY TESTS

I) Efficacy for human immunodeficiency virus (HIV) in cell culture

To test the inhibitory effect of various combination products on the replication of HIV, lymphocytes were isolated from fresh human blood by gradient centrifugation, stimulated by addition of phytohemagglutinin (active compound based on N-acetylgalactosamine and obtained from Phaseolus vulgaris) in RPMI 1640 medium (cell culture substrate, mixture of amino acids, vitamins, minerals and buffer substances, cf. G. E. Moore et al. J.A.M.A. 199, 519 (1967)) containing 10% fetal calf serum, and then cultivated in complete RPMI medium (complete RPMI medium = RPMI 1640 + calf serum) containing 20 I.U./ml recombinant interleukin-2 (Kulitz et al. Drug Res. 35, 1607 (1985)) at 37° C. for three days. Single portions of the stimulated lymphocytes were dispensed into containers and stored in liquid nitrogen. For the experiments, cells were thawed and cultivated in complete RPMI medium with recombinant interleukin-2 for three to four days. For the infection, the cells were mixed with the cell-free supernatant from HIV-infected cell cultures and incubated for 30 minutes. The infected cells were washed once and then taken up in complete RPMI medium with interleukin-2, to which the test substance was added in appropriate concentration, and inoculated in 24-well plates. After incubation at 37° C. for 3 days, half the medium was removed in each case and replaced by fresh medium containing active substance. The cell cultures were evaluated on the fourth day after the infection by inspection under the microscope. The degree of virus replication was estimated on the basis of the number and size of the syncytia. The concentration of each of the active substances is entered in Table 1, and a note is made for each composition about whether inhibition of syncytium formation was observed or not. Table 1 shows that inhibition of syncytium formation can be achieved with all the investigated sulfated polysaccharides by adding a defined amount of xanthine derivative to an amount of sulfated polysaccharide which is ineffective on administration alone. This demonstrates the increase in efficacy of the sulfated polysaccharides by addition of xanthine derivative.

TABLE 1

| Component a) | Concentration μg/ml | Component b) | Concentration μg/ml | Inhibition of syncytium formation |
|---|---|---|---|---|
| Levan poly-sulfate, Na salt, Mean molecular weight 8,000 Dalton, Degree of sulfation 100% | 10 | Pentoxi-fylline | — | no |
| | 20 | | — | no |
| | 50 | | — | yes |
| | 10 | | 5 | no |
| | 10 | | 25 | no |
| | 10 | | 100 | no |
| Levan poly-sulfate, Na salt, Mean molecular weight 8,000 Dalton, Degree of sulfation 100% | 25 | Pentoxi-fylline | 5 | no |
| | 25 | | 25 | yes |
| | 25 | | 100 | yes |
| | | | 100 | no |
| Dextran poly-sulfate, Na salt, Mean molecular weight 8,000 Dalton, Degree of sulfation 80% | 10 | Pentoxi-fylline | 5 | no |
| | 10 | | 25 | no |
| | 10 | | 100 | no |
| | 25 | | 5 | no |
| | 25 | | 25 | no |
| | 25 | | 100 | yes |
| | — | | 100 | no |
| Pentosan poly-sulfate SP 54, Na salt, Mean molecular weight 6,000 Dalton, Degree of sulfation 90% | 10 | 1-(5-hydroxy-hexyl)-3-methyl-7-propylxanthine | 5 | no |
| | 10 | | 25 | no |
| | 10 | | 100 | yes |
| | — | | 100 | no |
| Pentosan poly-sulfate SP 54, Na salt, Mean molecular weight 6,000 Dalton, Degree of sulfation 90% | — | Pentoxi-fylline | 100 | no |
| | 5 | | — | no |
| | 5 | | 1 | no |
| | 5 | | 10 | no |
| | 5 | | 100 | no |
| | 10 | | — | no |
| | 10 | | 1 | no |
| | 10 | | 10 | yes |
| | 10 | | 100 | yes |

TABLE 1-continued

| Component a) | Concentration μg/ml | Component b) | Concentration μg/ml | Inhibition of syncytium formation |
|---|---|---|---|---|
| Pentosan polysulfate SP 54, Na salt, Mean molecular weight 6,000 Dalton, Degree of sulfation 90% | 25 25 25 25 — | Pentoxifylline | — 1 10 100 100 | yes yes yes yes no |

II) Efficacy of pentosan polysulfate (SP 54) for retrovirus infections in the mouse Since no suitable infection model in laboratory animals exists for HIV infection in humans, it is necessary to have recourse to infections with other retroviruses for testing chemotherapeutic agents. Where the inhibition of virus replication in vivo is investigated on the basis of specific blocking of RT activity, it appears justified to choose a substitute model of this type. Infection of the mouse with Friend leukemia virus was chosen in the present case.

For this purpose, normal laboratory mice (NMRI=Naval Medical Research Institute) were infected by intravenous injection with mouse serum containing Friend virus. In the untreated control animals a distinct enlargement of the spleen and liver developed within two weeks as a sign of the infection. Treatment lasted 10 days, starting 48 hours after the infection. On day 14 of the experiment, the animals were sacrificed by luxation of the cervical vertebrae and opened up. The spleen was removed and weighed. The weight of the spleen of the treated animals was related to that of the untreated infection control as a parameter to measure the therapeutic efficacy.

Whereas the spleen of uninfected fully grown laboratory mice (20–24 g body weight) weighed less than 1% of the body weight, the spleen of infected animals reached about 10% of the body weight at the end of the experiment. Treatment with suramin resulted in a reduction in the growth of the spleen, and this reduction was mostly confirmed statistically (p<0.05). Pentosan polysulfate when administered alone also showed a distinct effect. Dextran polysulfate, administered alone and in combination with pentoxifylline, was likewise effective in the animal model investigated, no comparison with pentosan polysulfate being possible because of the relatively small number of animals. Combined administration of pentosan polysulfate and pentoxifylline diminished the degree of splenomegaly (swelling of the spleen) compared with treatment with pentosan polysulfate alone. Pentoxifylline exerted no effect on the course of the infection.

The relatively high mortality of the mice on administration of pentosan polysulfate was attributable to hemorrhages following the puncture injuries on injection of the medicaments, which often occurs in smaller experimental animals. In larger experimental animals and in humans, the risk of bleeding to death from a puncture injury from an injection needle is negligible.

TABLE 2

Theraputic effect of pentosan polysulfate (SP 54) in combination with pentoxifylline (Trental) on Friend virus infection of mice

| Product | Dosage | Rel. spleen weight % of body weight | Survivors/ group size | Significance |
|---|---|---|---|---|
| Control | — | 9.22 ± 2.76 | 7/7 | 1.0 |
| Suramin | 10 × 1.0 mg | 4.8 ± 0.96 | 7/7 | <0.05 |
| Pentosan polysulfate | 20 × 0.25 mg | 5.67 ± 2.85 | 7/7 | 0.017 |
| Pentosan polysulfate | 20 × 1.0 mg | 5.88 ± 3.40 | 2/7 | 0.094 |
| Pentoxifylline | 20 × 0.04 mg | 8.32 ± 1.45 | 7/7 | 0.232 |
| Pentoxifylline | 20 × 0.4 mg | 9.45 ± 2.0 | 7/7 | 0.428 |
| Pentoxifylline | 20 × 1.0 mg | 9.08 ± 2.36 | 7/7 | 0.459 |
| Pentosan polysulfate + Pentoxifylline | 20 × 0.25 mg  20 × 0.04 mg | 5.07 ± 2.1 | 5/7 | 0.009 |
| Pentosan polysulfate + Pentoxifylline | 20 × 0.25 mg  20 × 0.04 mg | 2.69 ± 1.67 | 3/7 | 0.03 |

We claim:

1. A pharmaceutical composition comprising at least one sulfated polysaccharide and at least one xanthine derivative selected from the group consisting of the following compounds:

a) compounds of the formula I

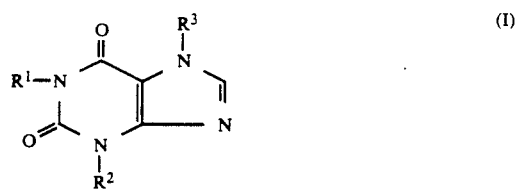

in which one of the radicals $R^1$ and $R^3$ represents a straight-chain alkyl, ($\omega$-1)-oxoalkyl or ($\omega$-1)-hydroxyalkyl group having 3 to 8 carbon atoms, an the two other radicals $R^2$ and $R^3$, or $R^1$ and $R^2$, represent straight-chain or branched alkyl groups having 1 to 8 carbon atoms in the position of $R^1$ and $R^3$, and 1 and 4 carbon atoms in the position of $R^2$, with the total of carbon atoms in these two alkyl substituents being not more than 10;

b) compounds of the formula II

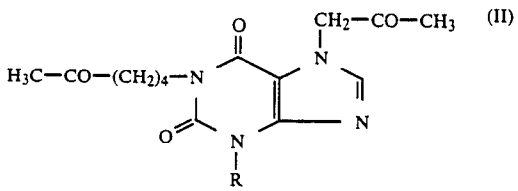

in which R represents an alkyl radical having 1 to 4 carbon atoms;

c) compounds of the formula III

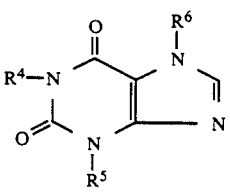

in which at least one of the radicals $R^4$ and $R^6$ represents a tertiary hydroxyalkyl group of the formula

where $R^7$ denotes an alkyl group having up to 3 carbon atoms, and n denotes an integer from 2 to 5 and, if only one of the radicals $R^4$ or $R^6$ denotes a tertiary hydroxyalkyl group of the formula IIIa, the other radical represents a hydrogen atom or an aliphatic hydrocarbon radical $R^8$ which has up to 6 carbon atoms and whose carbon chain can be interrupted by up to 2 oxygen atoms or substituted by an oxo group or up to two hydroxyl groups, and $R^5$ represents an alkyl group having 1 to 4 carbon atoms;

d) prodrug forms of the compounds of the formulae I to III; and e) metabolites of the compounds of the formulae I to III.

2. A composition as claimed in claim 1, wherein said at least one sulfated polysaccharide is selected from the group consisting of dextran polysulfate, levan polysulfate and pentosan polysulfate.

3. A composition as claimed in claim 2, wherein said at least one sulfated polysaccharide is pentosan polysulfate.

4. A composition as claimed in claim 1, wherein said at least one sulfated polysaccharide has a molecular weight of from about 1,000 to about 200,000 Dalton.

5. A composition as claimed in claim 4, wherein said at least one sulfated polysaccharide has a molecular weight of from about 5,000 to about 12,000 Dalton.

6. A composition as claimed in claim 1, wherein said at least one sulfated polysaccharide has a degree of sulation of the polysaccharide OH groups of from about 20 to 100%.

7. A composition as claimed in claim 6, wherein said at least one sulfated polysaccharide has a degree of sulfation of the polysaccharide OH groups of from about 50 to about 95%.

8. A composition as claimed in claim 7, wherein said at least one sulfated polysaccharide has a degree of sulfation of the polysaccharide OH groups of about 90%.

9. A composition as claimed in claim 1, wherein said at least one xanthine derivative is selected from the group consisting of the following compounds:
1-hexyl-3,7-dimethylxanthine,
1-(5-hydroxyhexyl)-3,7-dimethylxanthine,
3,7-dimethyl-1-(5-oxohexyl)xanthine,
7-(5-hydroxyhexyl)-1,3-dimethylxanthine,
1,3-dimethyl-7-(5-oxohexyl)xanthine,
1-(5-hydroxyhexyl)-3-methyl-7-propylxanthine,
3-methyl-1-(5-oxohexyl)-7-propylxanthine, and 7-ethoxymethyl-1-(5-hydroxy-5-methylhexyl)-3-methyl-xanthine.

10. A composition as claimed in claim 9, wherein the xanthine derivative is 3,7-dimethyl-1-(5-oxohexyl)-xanthine.

11. A composition as claimed in claim 1, wherein the ratio by weight of said at least one sulfated polysaccharide to said at least one xanthine derivative is between about 1:10 and about 100:1.

12. A composition as claimed in claim 11, wherein the ratio by weight of sulfated polysaccharide to xanthine derivative is between about 1:10 and about 30:1.

13. A process for preparing a pharmaceutical composition as claimed in claim 1, comprising converting at least one sulfated polysaccharide with at least one xanthine derivative into a suitable dosage form.

14. A process as claimed in claim 13, wherein the sulfated polysaccharide and xanthine derivative are converted together with further additives and/or auxiliaries into a suitable dosage form.

* * * * *

UNITED STATES PATENT AND TRADEMARK OFFICE
CERTIFICATE OF CORRECTION

PATENT NO. : 5,055,457
DATED : October 08, 1991
INVENTOR(S) : Elmar Schrinner et al.

It is certified that error appears in the above-identified patent and that said Letters Patent is hereby corrected as shown below:

Front Page, Title, change "COMBINATIONS" to --COMBINATION--.
Claim 1, column 10, line 61, change "an" to --and--.
Claim 1, column 10, line 65, before "4" change "and" to --to--.
Claim 6, column 12, line 12, change "sulation" to --sulfation--.

Signed and Sealed this

Twenty-seventh Day of April, 1993

Attest:

MICHAEL K. KIRK

*Attesting Officer*  Acting Commissioner of Patents and Trademarks